United States Patent [19]

Houpt et al.

[11] Patent Number: 4,711,126
[45] Date of Patent: Dec. 8, 1987

[54] SENSOR FOR THE MEASUREMENT OF THE REFRACTIVE INDEX OF A FLUID AND/OR PHASE BOUNDARY BETWEEN TWO FLUIDS BY MEANS OF VISIBLE OR INVISIBLE LIGHT

[75] Inventors: Pieter M. Houpt; Ralph T. Wielandt, both of The Hague, Netherlands

[73] Assignee: 501 Nederlandse Centrale Organisatie Voor Toegepast-Enschappelijk Onderzoek, The Hague, Netherlands

[21] Appl. No.: 838,675

[22] Filed: Mar. 12, 1986

[30] Foreign Application Priority Data

Mar. 13, 1985 [NL] Netherlands .......................... 8500726
Oct. 8, 1985 [NL] Netherlands .......................... 8502744

[51] Int. Cl.⁴ ............................................. G01F 23/28
[52] U.S. Cl. .................................... 73/293; 250/577; 429/91
[58] Field of Search ............................ 73/293; 429/91

[56] References Cited

U.S. PATENT DOCUMENTS

| 3,054,291 | 9/1962 | Landwer | 250/577 X |
| 3,602,037 | 8/1971 | Neu | 73/293 X |
| 3,669,772 | 6/1972 | Strack | 350/96.29 X |
| 3,895,964 | 7/1975 | Sakamoto | 429/91 |
| 4,045,668 | 8/1977 | Pitt et al. | 250/227 |
| 4,287,427 | 9/1981 | Scifres | 250/577 |
| 4,320,291 | 3/1982 | Uramoto | 250/227 |
| 4,342,919 | 8/1982 | Brogardh | 250/577 |

FOREIGN PATENT DOCUMENTS 1463910 2/1977 United Kingdom .................. 73/293

OTHER PUBLICATIONS

Patent Abstracts of Japan, vol. 5, No. 157 (P-83) (829) Oct. 8, 1981 Japanese Patent application 56 90 244 (Nippon ITA Glass K.K.) 22-07-1981 "The whole article".

Primary Examiner—Daniel M. Yasich
Attorney, Agent, or Firm—Brumbaugh, Graves, Donohue & Raymond

[57] ABSTRACT

A sensor for the measurement of the refractive index of a fluid and/or phase boundary between two fluids comprises a light guide in the form of a rod; one end of the rod is connected to both a light source and a detection element and the other end of the rod is reflective. If the sensor is used in a refractive index gauge the measurement should be independent of the liquid level; if the sensor is used in a level gauge, a digital measurement should be possible. The coating is provided with one or more cut-outs consisting of windows which are in direct contact with the surrounding fluid.

17 Claims, 2 Drawing Figures

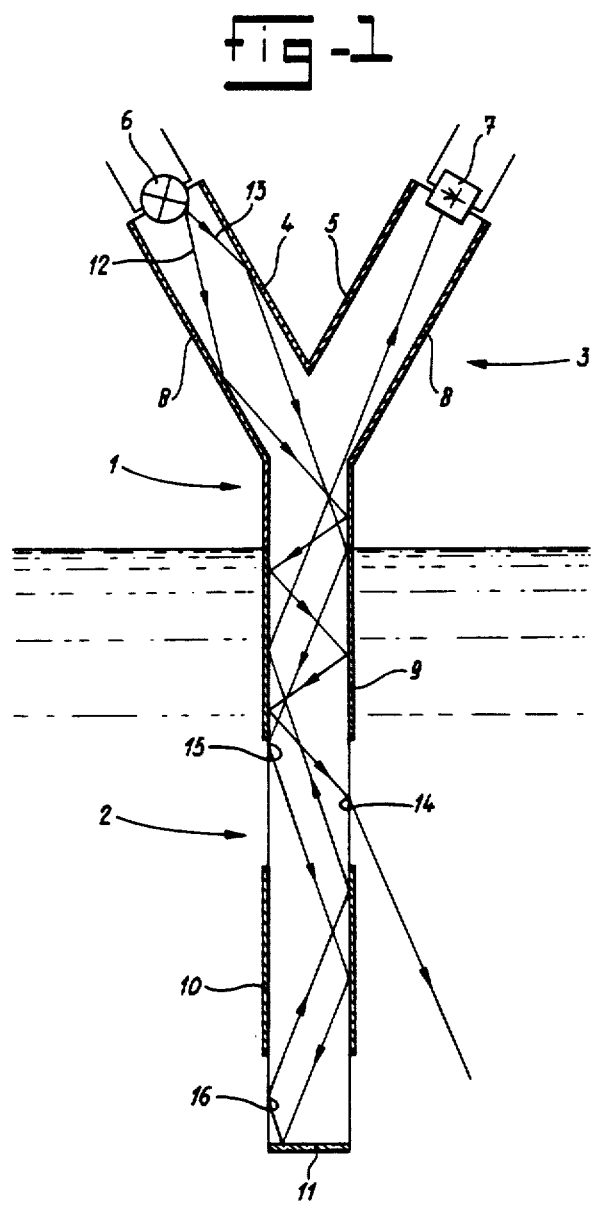

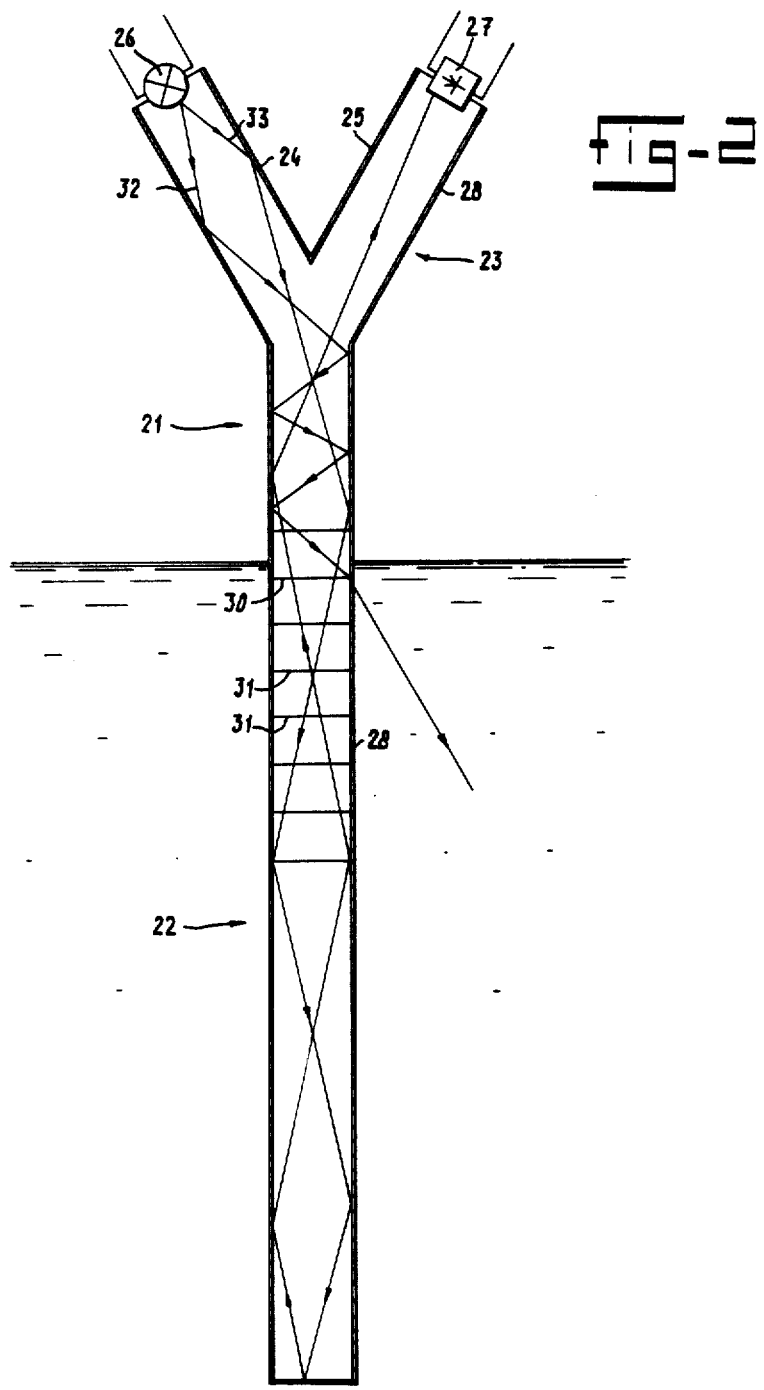

SENSOR FOR THE MEASUREMENT OF THE REFRACTIVE INDEX OF A FLUID AND/OR PHASE BOUNDARY BETWEEN TWO FLUIDS BY MEANS OF VISIBLE OR INVISIBLE LIGHT

BACKGROUND OF THE INVENTION

The invention relates to a sensor for the measurement of the refractive index of a fluid and/or the phase boundary between two fluids with visible or invisible light, which sensor comprises a light guide in the form of a rod with a refractive index greater than that of the fluid or fluids respectively, one end of the rod being connected to both a light source and a detection element sensitive to reflected light and the other end of the rod being reflective, and a cladding around the rod being provided with one or more cut-outs.

A sensor of this type is described in the German Offenlegungsschrift No. 3,012,328.

It is known that the refractive index of a fluid changes with the density of the said fluid and that the concentration of an acid in solution can be determined on the basis of a refractive index measurement, which may, for example, be of importance in the continuous or discontinuous monitoring of the state of charge of a battery in which sulphuric acid is used as electrolyte. A sensor of this type is described in "Patents Abstracts of Japan" vol. 5, No. 157, page 83 (829), Oct. 8, 1981. This known sensor is provided with a reflective membrane only at its end face projecting into the liquid, the cladding of the rod which consists of a super-transparent quartz glass is not coated. A disadvantage of this sensor is that a sufficiently accurate measuremnet can be achieved only if the liquid level remains constant.

Moreover, it is known that the position of a liquid level in a tank or vessel can be determined by measuring the light which is lost through openings in the cladding of a light guide which is inserted into the liquid. A measurement device which is suitable for this purpose is described in the said German Offenlegungsschrift 3,012,328. The sensor used in the latter is constructed in the form of an optical fibre with a refractive index greater than that of the surroundings. One end of the fibre is connected to a light source and to a detection element which is sensitive to reflected light, while the other end of the rod is reflecting. Around the fibre there is disposed a cladding, the refractive index of which is lower than that of the fibre. The cladding is provided with one or more long cut-outs which extend with their longitudinal direction in the axial direction of the fibre. Opposite the cut-outs there is located a light absorbing plastic-material film which is pressed in the liquid by hydrostatic pressure against the cut-out. Due to the presence of the light-absorbing film this sensor is certainly relatively insensitive to contamination, but disadvantages are the vulnerability, the complexity and the fact that only analogue (not digital) measurements can be made with the result that, for example, a drift in the electronic section of the device results in inaccuracies.

SUMMARY OF THE INVENTION

The object of the invention is to avoid the disadvantages of the said known sensors and to provide a sensor of the type indicated in the introduction which, if used in a refractive index gauge, makes the measurement independent of the liquid level and, if used in a level gauge, permits a digital measurement, and as a result eliminates in a simple and cheap manner the disturbing effect of contamination and the drift of the electronic section.

According to the invention the specified cladding for this purpose consists of a coating of reflective material bonded to the surface of the rod, and the cutouts consist of windows which are in direct contact with the surrounding fluid.

When used in a refractive gauge, the possibility is not excluded that there is only one window which is always below the level of the liquid. However, in general it is preferable that a number of windows are provided with a mutual distance in the axial direction of the rod. By having windows over large sensor lengths data are obtained on the refracted index of the entire liquid and not only at the point of the sensor. After all, the density of a liquid, and consequently of the refractive index, usually varies from position to position and these differences do not necessarily proceed in accordance with a certain or known gradient.

When used as a level gauge, a number of windows above each other is even a precondition for digital measurements to be possible. The windows then consist preferably of openings of low height, for example thin rings. When a ring passes through the liquid level, a stepwise change in the detection element signal is measured. The number of steps is a measure of the height of the liquid level. This measurement is virtually insensitive to contamination.

If the windows have a different surface area, it is possible to perform an absolute measurement, i.e. from the size of the step in the signal, it is possible to determine which window has been passed. The operation of sensors is in fact based on the phenomenon that, of the light which is radiated into the light guide, more is lost if windows come to rest in the phase with the larger refractive index. When the separation between the phases shifts, i.e. in the case of a liquid, when the liquid level falls or rises, as each window passes through the separation or the liquid level, a step will occur in the light loss and consequently in the signal given by the detection element. The polarity of the signal step is determined by the direction of the crossing. If the signal is differentiated twice electronically, signal pulses are produced, the polarity of which corresponds to the direction of change of the liquid level. After calibrating the liquid level can be registered in this manner with an electrical pulse counter. In the case of windows with a different surface area this method of calculation (double differentiation etc.) to obtain signal pulses is not necessary.

One and the same sensor may be used for the measurement of a liquid level and for the determination of the refractive index, in which case, of a series of windows situated at a distance from each other in the axial direction, only the uppermost windows are used for the determination of the position of the liquid level and the other windows for the determination of the refractive index.

Preferably the sensor is fork-shaped, the light source and the detection element each being situated on one of the two arms of the fork, while the other end of the rod is provided with a reflective layer. The light source and the detection element may then be located outside the liquid.

Attack by a surrounding aggressive fluid is no longer to be feared if the coating is a gold layer. If infra-red light is used, a gold layer also has particular advantages because of the high reflection coefficient for the light.

The invention relates also to a rechargeable battery, in particular a lead/sulphuric acid cell with builtin sensor according to one or more of the abovenamed characteristics.

BRIEF DESCRIPTION OF THE DRAWINGS

The invention may be better understood from the following detailed description, taken in conjunction with the accompanying drawings in which:

FIG. 1 is a side cross-sectional view of an embodiment of a sensor for measuring the refractive index of a fluid, and FIG. 2 is a side cross-sectional view of an embodiment of a sensor for measuring the level of a fluid.

DESCRIPTION OF THE PREFERRED EMBODIMENTS

The embodiment according to FIG. 1 is intended in particular for the measurement of the refractive index of a fluid, which measurement is usually used for the determination of the density of a fluid, for example the concentration of a substance in solution.

Part 2 of the fork-shaped measuring device 1 shown in the figure is immersed in a fluid such as sulphuric acid. Part 3 of this measuring device projects above the level of the fluid and comprises two arms 4 and 5. At the end of arm 4 there is disposed a light source 6, while arm 5 is provided with a detection element 7 at its extremity. The measuring device 1 is provided with a reflective layer 8 in the case of the part 3 projecting above the sulphuric acid, while the part located in the liquid is provided with two reflective coatings 9 and 10 which extend over the whole circumference of the rod. At the extremity immersed in the liquid the measurement device 1 is provided with a specular layer 11. How the light rays 12 and 13 respectively exit from the light source 2 is shown. The angle of incidence of the light ray 12 on the wall of part 2 is smaller than the critical angle with the result that at the point 14, where there is no reflective layer, this light ray will pass outwards into the fluid diverging from the normal. The angle which the light ray 13 makes with the part 2 of the rod is greater than the critical angle with the result that at position 15 and 16 reflection will occur and the reflected light will strike the detection element 7. If the refractive index between the measuring device and the fluid surrounding this measuring device becomes smaller, i.e. in the case of sulphuric acid the density becomes smaller, the critical angle will become smaller, which means that more light will be reflected. This is detected by the detection element 7 and can be read out by devices which are constructed according to the prior art. By providing the part 2 of the device 1 immersed in the fluid with a reflective coating 9, 10 at various positions, the density of the fluid can be measured at a number of positions. As a result of measuring at various positions, the signal registered by the detection element 7 is a mean of the density of the sulphuric acid at the said different positions. The reflective coatings 9, 10 are preferably of gold which combines a good reflection with a corrosion-resistant character with respect to the sulphuric acid. If infra-red radiation is used gold is of particularly advantage. It is obviously also possible not to provide the part 2 of the measuring device 1 immersed in the fluid with a reflective coating with the exception of the uppermost section with the result that a mean measurement of the density of the sulphuric acid in which the rod is immersed is performed. The part 3 of the measuring device 1 projecting above the fluid is provided with a reflective layer 8 to prevent light already passing outwards in the legs, which would mean an undesired loss. The light radiated by the light source 6 may comprise monochromatic light, various parts of the light spectrum as well as all other electromagnetic waves.

The embodiment depicted is not restrictive. Thus, the light source and the detection element can be placed next to each other in a different manner, while the part immersed in the fluid may also have a different shape such as a curved shape. The light source may be a point source or may be such that a beam of directed light is emitted.

Because the light can exit at different parts of the cladding surface of the section projecting into the fluid, the measurement of the refractive index is not limited to a certain position in the liquid but may extend over a certain height. If the refractive index gauge is used to determine the density or concentration of an acid, a very accurate result can be achieved for the state of density or concentration in the entire liquid. The registration or concentration in the entire liquid. The registration of the refractive index, or of the density or concentration can take place continuously or discontinuously. The refractive index measurement is independent of the liquid level.

The embodiment according to FIG. 2 is intended in particular for the measurement of the level of a liquid in a tank or vessel. The part 22 of the fork-shaped sensor 21 depicted in this figure is immersed in a fluid such as sulphuric acid. The part 23 of this sensor projects above the level of the fluid and comprises two arms 24 and 25. At the end of the arm 24 there is disposed a light source 26, while arm 25 is provided with a detection element 27 at its extremity. The sensor 21 is covered with a reflective coating 28, preferably a gold layer. The latter also covers the end immersed in the liquid. In the section of the reflective layer which covers the cladding of the part 22 annular windows 31 in the form of thin rings cut out of the reflective coating are milled at a mutual distance (for example 5 mm). The width of the windows is, for example, 100 micrometre. How the two light rays 32 and 33 respectively emerge from the light source is depicted. The angle of incidents of the light ray 32 on the wall of part 22 is smaller than the critical angle with the result that when incident on a window 30 where no reflective layer is present, this light ray will pass outwards into the fluid diverging from the normal. The angle of incidence which the light ray 33 has in relation to the wall of the part 22 of the rod is greater than the critical angle, with the result that when incident on a window 31, only reflection occurs and the reflected light strikes the detection element 27. If, as a result of drop in the liquid level, a window 31 is surrounded by air instead of by liquid, the critical angle will become considerably smaller, which means that more light will be reflected and less light will end up outside the rod as a result of refraction. If the liquid level falls, the detection element 27 will record stepwise an increase of reflected light, while if the liquid level rises, a stepwise reduction of reflected light is detected. The polarity can be determined by the direction of the step. This method is particularly suitable for digital measurement.

The windows 31 could possess mutually differing surface areas with the result that from the size of the signal step recorded by the detection element 27 it should be possible to determine which window 31 is passed by the liquid level. A further correction may be necessary for the change in the refractive index of the surrounding liquid. If the windows all have the same width, the signal steps will possess the same magnitude. By differentiating the signal twice pulses are produced, the polarity of which corresponds to the direction of change of the liquid level. The absolute liquid level can thus be recorded after calibration with an electrical pulse counter.

The essential point is that the loss of light is measured in the case that more or less windows are surrounded by a medium (for example liquid) of larger refractive index. This principle is used to determine the acid level in a lead/sulphuric acid cell but also to determine the position of the separation between different phases in different vessels, tanks or holders.

The possibility is not excluded that the sensors described above are combined, the upper windows consisting of thin rings for the determination of the liquid level and the lower windows being much larger and intended for the determination of the refractive index of the medium into which the sensor projects. The liquid level is determined by means of the number of steps, while the density is determined by means of the absolute magnitude of the measurement itself (possibly corrected for liquid level).

The rings have very small dimensions in the longitudinal direction of the sensor, i.e. in the direction of movement of the liquid level. These dimensions are smaller than the desired accuracy of level detection.

The sensors described are robust, simple and not vulnerable. A level measurement performed therewith is not sensitive to contamination and drift of the electronic section of the measuring device. For the various embodiments, it is always essential that the cladding on the sensor consists of a coating of reflective material bonded to the surface of the rod and that windows are provided in said coating which are in contact directly with the surrounding fluid.

We claim:

1. A rechargeable battery comprising a rechargeable fluid-containing cell and a sensor for obtaining measurements of at least one fluid associated with said cell, the sensor comprising
    a light guide having a refractive index greater than that of the fluid, the light guide being a fork-shaped rod having a portion at one end thereof adapted for immersion in the fluid, the opposite end of the rod being adapted for connection thereto a light source for directing visible or invisible light into the light guide and means for detecting reflected light,
    a cladding bonded to the peripheral surface of the rod, the cladding comprising a coating of reflective material, and
    one or more window cut outs in the reflective coating bonded to the portion of the rod adapted for immersion in the fluid, whereby when the rod is immersed, the windows are in direct contact with the fluid.

2. Rechargeable battery according to claim 1 in which the battery is a lead/sulfuric acid cell.

3. A rechargeable battery comprising a rechargeable fluid-combining cell and a sensor for obtaining measurements of at least one fluid associated with said cell, the sensor comprising
    a light guide having a refractive index greater than that of the fluid, the light guide being a fork-shaped rod having a portion thereof adapted for immersion in the fluid,
    a cladding bonded to the peripheral surface of the rod, the cladding comprising a coating of reflective material,
    a light source for directing visible or invisible light into the light guide connected to an end of the rod not adapted for immersion in the fluid,
    means for detecting reflected light also connected to the end of the rod not adapted for immersion in the fluid, and
    one or more window cut-outs in the reflective coating bonded to the portion of the rod adapted for immersion in the fluid, whereby when the rod is immersed the windows are in direct contact with the fluid.

4. Rechargeable battery according to claim 3 in which the battery is a lead/sulfuric acid cell.

5. A sensor for obtaining measurements of at least one fluid in a chamber, the sensor comprising
    a light guide having a refractive index greater than that of the fluid, the light guide being a fork-shaped rod having a portion thereof adapted for immersion in the fluid,
    a cladding bonded to the peripheral surface of the rod, the cladding comprising a coating of reflective material,
    a light source for directing visible or invisible light into the light guide connected to an end of the rod not adapted for immersion in the fluid,
    means for detecting reflected light also connected to the end of the rod not adapted for immersion in the fluid, and
    one or more windows cut-outs in the reflective coating bonded to the portion of the rod adapted for immersion in the fluid, whereby when the rod immersed, the windows are in direct contact with the fluid.

6. A sensor according to claim 5 for measuring the refractive index of the fluid wherein the windows extend over large portions of the length of the rod adapted for immersion and are so positioned in the reflective coating such that, when the sensor is in use, all windows are located below the surface of the fluid in which the rod is immersed, whereby a measurement of the refractive index independent of local variations in the refractive index of the fluid and the level of the fluid is obtained.

7. A sensor according to claim 5 for measuring the level of the fluid in the chamber wherein the windows are of low height and are so positioned in the reflective coating covering the portion of the rod adapted for immersion that when the sensor isin use, the windows are located both above and below the level of the fluid, whereby upon a change in the level, light slot through each window as it passes through the level of the fluid generates a signal, in the means for detecting reflected light.

8. A sensor according to claim 7 in which the windows are thin rings cut out of the reflective coating.

9. A sensor according to claim 7 in which each window has a different surface area.

10. A sensor according to claim 5 in which the windows are mutually distant from each other in the axial direction of the rod.

11. A sensor according to claim 5 in which the reflective material is gold.

12. A sensor for simultaneously measuring both the refractive index and the level of a fluid in a chamber, the sensor comprising
- a light guide having a refractive index greater than that of the fluid, the light guide being a fork-shaped rod having a portion thereof adapted for immersion in the fluid,
- a cladding bonded to the peripheral surface of the rod, the cladding comprising a coating of reflective material,
- a light source for directing visible or invisible light into the light guide connected to an end of the rod not adapted for immersion in the fluid,
- means for detecting reflected light also connected to the end of the rod not adapted for immersion in the fluid, and
- one or more window cut outs in the reflective coating bonded to the portion of the rod adapted for immersion in the fluid, the windows being mutually distant from one another in the axial direction of the rod, and the windows in an upper part of the rod portion being in the form of thin rings while the windows in the lower part of the rod portion extend over large distances in the rod, whereby when the rod is immersed the windows are in direct contact with the fluid.

13. A sensor according to claim 12 in which the reflective coating is gold.

14. A sensor for obtaining measurements of at least one fluid in a chamber the sensor comprising
- a light guide having a refractive index greater than that of the fluid, the light guide being a fork-shaped rod having two upper arms and a lower portion adapted for immersion into the fluid,
- a cladding bonded to the peripheral surface of the rod, the cladding comprising a coating of reflective material,
- a light source for directing visible or invisible light into the light guide connected to one of the upper arms of the rod,
- means for detecting reflected light connected to the second upper arm of the rod, and
- one or more window cut outs in the reflective coating in the lower portion of the rod, whereby when the rod is immersed the windows are in direct contact with the fluid.

15. A sensor according to claim 14 in which the reflective coating is gold.

16. A sensor for obtaining measurements of at least one fluid in a chamber, the sensor comprising
- a light guide having a refractive index greater than that of the fluid, the light guide being a fork-shaped rod having a portion at one end thereof adapted for immersion in the fluid, the opposite end of the rod being adapted for connection thereto a light source for directing visible or invisible light into the light guide and means for detecting reflected light,
- a cladding bonded to the peripheral surface of the rod, the cladding comprising a coating of reflective material, and
- one or more window cut outs in the reflective coating bonded to the portion of the rod adapted for immersion in the fluid, whereby when the rod is immersed, the windows are in direct contact with the fluid.

17. Sensor according to claim 16 in which the reflective material is gold.

* * * * *

UNITED STATES PATENT AND TRADEMARK OFFICE
CERTIFICATE OF CORRECTION

PATENT NO. : 4,711,126

DATED : December 8, 1987

INVENTOR(S) : Pieter M. Houpt et al.

It is certified that error appears in the above-identified patent and that said Letters Patent is hereby corrected as shown below:

Title page, Item 73, "501 Nederlandse Centrale Organisatie Voor Toegepast-Enschappelijk Onderzoek" should read --Nederlandse Centrale Organisatie Voor Toegepast-Natuurwetenschappelijk Onderzoek--, Column 3, line 4, "builtin" should read --built in--.

Column 3, line 65, "particularly" should read --particular--.

Column 4, lines 25-26, delete "or concentration in the entire liquid. The registration";

Column 4, line 47, "incidents" should read --incidence--.

Column 6, line 37, "windows" should read --window--.

Column 6, line 56, "isin" should read --is in--.

Signed and Sealed this

Twenty-first Day of June, 1988

Attest:

DONALD J. QUIGG

Attesting Officer

Commissioner of Patents and Trademarks